(12) United States Patent
Albalat

(10) Patent No.: US 12,186,473 B2
(45) Date of Patent: Jan. 7, 2025

(54) FILTRATION APPARATUS

(71) Applicant: BIOSURGICAL S.L, Madrid (ES)

(72) Inventor: Alberto Martinez Albalat, Madrid (ES)

(73) Assignee: BIOSURGICAL S.L., Madrid (ES)

( * ) Notice: Subject to any disclaimer, the term of this patent is extended or adjusted under 35 U.S.C. 154(b) by 1311 days.

(21) Appl. No.: 16/347,941

(22) PCT Filed: Nov. 10, 2017

(86) PCT No.: PCT/EP2017/078951
§ 371 (c)(1),
(2) Date: May 7, 2019

(87) PCT Pub. No.: WO2018/087327
PCT Pub. Date: May 17, 2018

(65) Prior Publication Data
US 2019/0293521 A1      Sep. 26, 2019

(30) Foreign Application Priority Data
Nov. 11, 2016   (GB) ...................................... 1619165

(51) Int. Cl.
*A61M 1/36*      (2006.01)
*A61F 7/12*      (2006.01)
(Continued)

(52) U.S. Cl.
CPC ............... *A61M 1/369* (2013.01); *A61F 7/12* (2013.01); *B01D 29/52* (2013.01); *B01L 3/02* (2013.01);
(Continued)

(58) Field of Classification Search
CPC .. G01N 1/20; G01N 1/18; G01N 1/40; G01N 2001/2064; G01N 2001/4088; G01N 1/00;
(Continued)

(56) References Cited

U.S. PATENT DOCUMENTS 4,341,124 A     7/1982 Rodgers et al.
8,187,215 B2 *  5/2012 Helm, Jr. ............ A61M 1/3666
                                                 604/6.11

(Continued)

FOREIGN PATENT DOCUMENTS

CN          1569266 A       1/2005
CN        104815360 A       8/2015
(Continued)

OTHER PUBLICATIONS

International Search Report to corresponding PCT application PCT/EP2017/078951, dated Feb. 2, 2018, 6 pages.

*Primary Examiner* — Jason E Flick
(74) *Attorney, Agent, or Firm* — Ronald M. Kachmarik; Cooper Legal Group LLC

(57) ABSTRACT

An apparatus for monitoring cells, biological materials, and/or particles in a fluid flow system including a plurality of fluid sampling loops arranged substantially in parallel adapted to allow the fluid to enter each of the plurality of fluid sampling loops sequentially at different time intervals. Each of the plurality of fluid sampling loops includes at least one filtration element adapted to retain the cells, biological materials, and/or particles when the fluid passes through each of the plurality of fluid sampling loops.

23 Claims, 5 Drawing Sheets

(51) Int. Cl.
   *B01D 29/52* (2006.01)
   *B01L 3/02* (2006.01)
   *G01N 1/18* (2006.01)
   *G01N 1/20* (2006.01)
   *G01N 1/40* (2006.01)

(52) U.S. Cl.
   CPC ............... *G01N 1/18* (2013.01); *G01N 1/20* (2013.01); *G01N 1/40* (2013.01); *A61M 2205/75* (2013.01); *A61M 2210/1017* (2013.01); *G01N 2001/2064* (2013.01); *G01N 2001/4088* (2013.01)

(58) Field of Classification Search
   CPC .......... G01N 1/02; G01N 1/10; G01N 1/2035; B01D 29/52; B01D 29/00; B01D 29/50; A61M 1/369; A61M 2205/75; A61M 2210/1017; A61M 1/3603; A61M 1/36; A61M 2210/1021; A61M 1/3601; A61M 1/34; A61M 1/3621; A61M 1/3623; A61F 7/12; A61F 7/00
   See application file for complete search history.

(56) References Cited

U.S. PATENT DOCUMENTS

| | | | |
|---|---|---|---|
| 2007/0025883 A1* | 2/2007 | Tai | B01D 61/14 422/400 |
| 2013/0098839 A1 | 4/2013 | Helm, Jr. | |
| 2013/0168303 A1 | 7/2013 | Appling et al. | |
| 2014/0057340 A1 | 2/2014 | Yu et al. | |
| 2015/0362410 A1 | 12/2015 | Neftel | |

FOREIGN PATENT DOCUMENTS

| | | | | |
|---|---|---|---|---|
| EP | 2868361 A1 * | 5/2015 | ............ | B01D 29/52 |
| JP | S49-082776 U | 7/1974 | | |
| JP | S51-011479 U | 1/1976 | | |
| JP | S57-108736 A | 7/1982 | | |
| JP | 2008-538509 A | 10/2008 | | |
| JP | 2013-244439 A | 12/2013 | | |
| WO | 2006116327 A1 | 11/2006 | | |
| WO | 2008146132 A2 | 12/2008 | | |

* cited by examiner

FILTRATION APPARATUS

The present invention relates to an apparatus and method for monitoring cells, biological materials, and/or particles in a fluid flow system.

Monitoring of cells, biological material, and particles in fluid flow systems has become important in many fields of technology and it has thus far been challenging to study the characteristics of cell, biological material, and particles in these systems over time.

In the field of medicine, it has long been recognised that organic and irrigating fluid analysis can be used as a diagnostic tool. This analysis is based on physical, chemical, or biological identification techniques, of elements as disease markers and their quantification compared to previously established gold standards. Such analysis may be useful in the diagnosis of different diseases based on the abnormal presence of metabolites, blood cells, proteins, pathologic microorganisms or even tumour cells, but also in irregular amounts or concentrations of the mentioned elements compared to predetermined standards.

One example of this type of analysis is urine cytology in which the presence of tumour cells in urine is determined by collection of a urine sample, performing cytocentrifugation, and identification of the presence or absence of tumour cells by microscopy. This type of analysis has been used not only for diagnosis but also as a predictive methodology to determine the stage of tumour cells growth. The disadvantages of this type of methodology are that it is labour intensive, known to produce false-positive and false-negative results and not applicable to all types of tumour cell.

Presence of tumoral cells in ascetic fluid has also been described as sign of advanced stages of cancer and a sign of an evolving cancer within the abdominal cavity.

The use of heat as a treatment of certain cancers, commonly known as hyperthermia, in combination with chemotherapeutic drugs has shown promising results in several clinical studies. However, hyperthermia treatment is an area of medicine that would greatly benefit from a new technique of monitoring disease progression and the effectiveness of the treatment.

Hyperthermia has been shown to have a therapeutic effect on killing tumour cells, as tumour cells are more sensitive and less resistant to temperature increase compared to normal cells. In addition, hyperthermia has been shown to alter the distribution of several drugs, for example by increasing drug absorption and tissue penetration. In particular, hyperthermia has been shown to increase drug uptake by neoplasic cells while at the same time inhibiting DNA repair in damaged neoplasic cells.

Bladder cancer may be treated by delivering cytotoxic drugs directly to the bladder of a patient. This type of treatment is known as intra-vesical chemotherapy. This technique delivers the cytotoxic drugs directly to the cancer cells with minimal absorption of the cytotoxic drugs into the patient's bloodstream. This means that intra-vesical chemotherapy is associated with higher effectiveness and fewer side effects than techniques that rely on the cytotoxic drugs circulating within the patient's bloodstream.

In intra-vesical chemotherapy, the cytotoxic drugs are delivered to a patient's bladder in the form of fluids via a catheter. In intra-vesical chemotherapy, a catheter is inserted via a patient's urethra and used to introduce chemotherapeutic drugs. The chemotherapeutic drugs circulating within the bladder may be heated to 41° C. to 44° C., preferably 43° C., to make the drugs more effective in killing the cancer cells.

The benefits of hyperthermia treatment have also been shown for peritoneal cancer. The peritoneum is the lining of the abdominal cavity. Tumour cells can spread to the peritoneum from organs such as the gastrointestinal tract and the ovaries. Standard chemotherapy techniques, such as systemic chemotherapy in which chemotherapy drugs are injected into the blood stream of a patient, present a limited efficacy in treating tumour cells in the peritoneum.

Hyperthermal intraperitoneal chemotherapy (HIPEC) is a chemotherapy treatment for peritoneal cancer performed after cytoreductive tumour surgery. HIPEC involves the circulation of a heated chemotherapeutic agent in the abdomen of a patient. The chemotherapeutic agent is highly concentrated and circulated at a temperature of about 41° C. to 44° C. for an average of 90 minutes to 120 minutes. The high temperature and concentration of the chemotherapeutic agent allow for penetration of the agent into the abdominal tissue in order to eliminate tumour cells not visible to a surgeon.

The combination of cytoreductive tumour surgery and HIPEC has been shown to increase 5 year survival rates and have minimal post operative mortality (Haslinger M, et al., A contemporary analysis of morbidity and outcomes in cytoreduction/hyperthermic intraperitoneal chemoperfusion. Cancer Med. 2013; 2(3):334-342).

At the present time, there is no means to determine the effectiveness of a hyperthermia treatment procedure or to determine the progression perspectives of tumour cell growth in the peritoneum at the time of performing the procedure. Today the efficacy is measured by the potential recurrence of the disease or its evolution after the treatment, and most of the therapeutic decisions are taken accordingly.

It is an object of the present invention to mitigate problems such as those described above.

According to a first aspect of the invention, there is provided an apparatus for monitoring cells, biological materials, and/or particles in a fluid flow system comprising a plurality of fluid sampling loops (i.e. two or more fluid sampling loops) arranged substantially in parallel adapted to allow the fluid to enter each of the plurality of fluid sampling loops sequentially at different time intervals, wherein each of the plurality of fluid sampling loops comprises at least one filtration element adapted to retain the cells, biological materials, and/or particles when the fluid passes through each of the plurality of fluid sampling loops. For example, fluid flows in the system and enters a first fluid sampling loop at $t=t_1$, then a second fluid sampling loop at $t=t_2$ etc., wherein $t_1$ is different from $t_2$.

This arrangement is advantageous as it provides an apparatus that can quickly, efficiently, and safely sample a fluid over different time points, without disturbing the regular procedure, to determine the characteristics of cells, biological materials, and/or particles in the fluid. The apparatus is also advantageous as fluid can be sampled at different time points as it continuously recirculates within a closed system and passes into and out, for example, a body cavity. The closed system provides a means to ensure that the body cavity is constantly washed with recirculating fluid during, for example, a hyperthermic recirculation fluid.

Preferably, each of the plurality of fluid sampling loops comprises at least one clamp and/or at least one valve adapted to allow fluid to enter a given sampling loop only at a predetermined time point. This provides a means for regulating when the fluid sampling loops are opened. Therefore, fluid can be sampled at various predetermined time points as the fluid sampling loops are opened individually and fluid from the fluid flow system allowed to flow through them. Within the context of this invention, it is envisaged to use any means suitable for allowing fluid to selectively enter a fluid sampling loop, at a selected time point. This redirection of the fluid flow can be effected manually or automatically.

Preferably, the apparatus comprises at least one clamp and/or at least one valve adapted to prevent reverse fluid flow in the plurality of sampling loops. Reverse flow through a fluid sampling loop is not desirable as it may wash cells, biological materials and particles out of the filtration element. These materials and particles might re-contaminate the fluid flow and/or any quantitative or qualitative measurement from the filtration element might be distorted. A means to prevent such reverse flow is therefore advantageous. Within the context of this invention, it is envisaged to use any means suitable for preventing reverse fluid flow towards the sampling loops.

Preferably, the system comprises an interface means adapted to allow connection and/or disconnection of the interface means from the fluid flow system without stopping a continuous flow and/or recirculation of the fluid in the fluid flow system. The apparatus enables samples to be taken without disrupting the flow of fluid in the fluid flow system. For example, in a recirculation system that flows fluid into and out from the body cavity of a patient, samples can be obtained at various time points without stopping the recirculation. Therefore, the procedure can continue as normal, without disrupting the treatment, while samples are taken and analysed in real time.

Preferably, the apparatus comprises a flushing means. A flushing means is advantageous as it allows the filtration elements to be washed to remove toxic and hazardous chemicals that may be used in the fluid flow system prior to analysis of the cells, biological materials, and particles retained by the filtration elements after filtering.

Preferably, the diameter of the plurality of filtration elements and/or the diameter of the pore size of the filtration elements is arranged in series increasing from a first filter of the plurality of filters to a last filter of the plurality of filtration elements. Monitoring may be quantitative or qualitative and the type of monitoring may depend upon the type of filtration element used in the apparatus. The filters in the filtration units may differ in diameter and therefore capacity to enable quantitative analysis or differ in their pore size to retain different sized cells, biological materials, and/or particles, or differ in the type of cell, biological materials, and/or particles that can be retained. However, in other embodiments of the invention, the filters in the plurality of filtration units may all be and have identical characteristics.

According to a second aspect of the invention, there is provided a filter element adapted for use with the apparatus of the first aspect of the invention.

According to a third aspect of the invention, there is provided a method of analysing cells, biological materials, and/or particles in a fluid flow system comprising sampling a fluid from the fluid flow system at different time points using a plurality of fluid sampling loops, wherein each of the fluid flow loops comprises a filtration element, wherein a given fluid sampling loop allows fluid to flow through that fluid sampling loop only at a predetermined time point selected for that fluid sampling loop. This method is advantageous as it provides a means to analyse cells, biological materials, and/or particles in a fluid flow system over time.

Embodiments of the present invention will now be described, by way of example, with reference to the accompanying drawings in which.

Figure 1A:
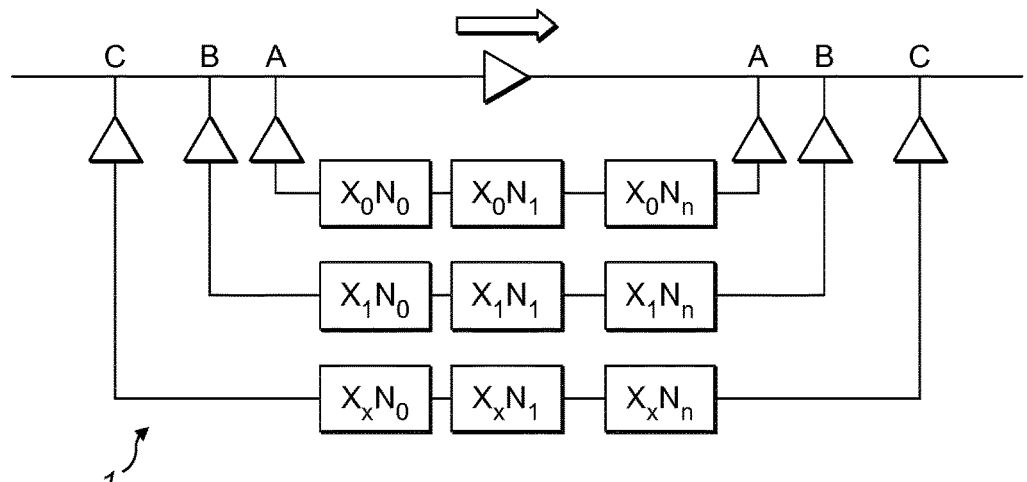
FIG. 1 is a schematic representation illustrating fluid flow through the apparatus of the present invention.

FIGS. 1A to 1D illustrate an apparatus 1 for monitoring cells, biological materials, and/or particles in a fluid flow system comprising a plurality of fluid sampling loops (A, B, and C) arranged substantially in parallel adapted to allow the fluid to enter each of the plurality of fluid sampling loops (A, B, and C) sequentially at different time intervals, wherein each of the plurality of fluid sampling loops (A, B, and C) comprises at least one filtration element ($X_0N_0$ to $X_xN_n$) adapted to retain the cells, biological materials, and/or particles when the fluid passes through each of the plurality of fluid sampling loops (A, B, and C).

The apparatus 1 of the present invention can be used to monitor fluid in a closed recirculation system. The fluid in the closed recirculation system can be monitored by using the filtration elements to filter the fluid. The fluid may be a therapeutic recirculation fluid. The recirculation of a therapeutic recirculation fluid in a body cavity can be used for therapeutic purposes in a number of ways, for example, monitoring cells, biological materials, and/or particles in the fluid. Cells, biological materials, and/or particles washed from a body cavity by the recirculation of the therapeutic recirculation fluid can be used to monitor the effectiveness of the therapy.

In a generic example of a fluid flow system, the system may comprise tubing or piping for containing and transporting the fluid and a pump to create the fluid flow. The system can be a closed recirculation system in which the system is adapted to create a fluid flow that recirculates the fluid into and out from a body cavity of a patient undergoing a procedure. The system may further comprise a heating and/or cooling means that can heat or cool the fluid as it recirculates into and out from the body cavity of a patient. Therefore, the fluid flow system may be used to produce hyperthermia or hypothermia fluids that recirculate in the fluid flow system into and out from the body cavity of a patient. The fluid flow system may further comprise a control system that controls the fluid flow system and/or the heating and/or cooling of the fluid in the fluid flow system. The fluid recirculating in the fluid flow system may be a liquid and the liquid may comprise a drug or therapeutic agent, for example a chemotherapeutic agent.

The fluid in the fluid flow system may be a hyperthermia treatment fluid. The hyperthermia treatment fluid may comprise a chemotherapeutic agent. This type of fluid is referred to as a hyperthermic chemotherapy treatment fluid The apparatus 1 of the present invention is particularly suited for determining the effectiveness of a hyperthermic chemotherapy treatment procedure and/or determining the progression of tumour cell growth in the body cavity at the time of performing a hyperthermic chemotherapy treatment procedure. During a hyperthermic chemotherapy treatment procedure, a highly concentrated and high temperature chemotherapeutic agent is recirculated within a body cavity of a patient, but is also applicable to other therapeutic procedures such as immunotherapy, radiotherapy, or just simply targeted diagnostic procedures. The steps of a standard hyperthermic chemotherapy treatment procedure are 1) the recirculation of a fluid in the body cavity prior to application of the chemotherapeutic agent, 2) application of the chemotherapeutic agent, and 3) flushing of the chemotherapeutic agent from the body cavity by recirculation of further fluid. The recirculation of the chemotherapeutic agent is performed in a closed system which pumps fluid in and out of a patient's body cavity.

Figure 7:
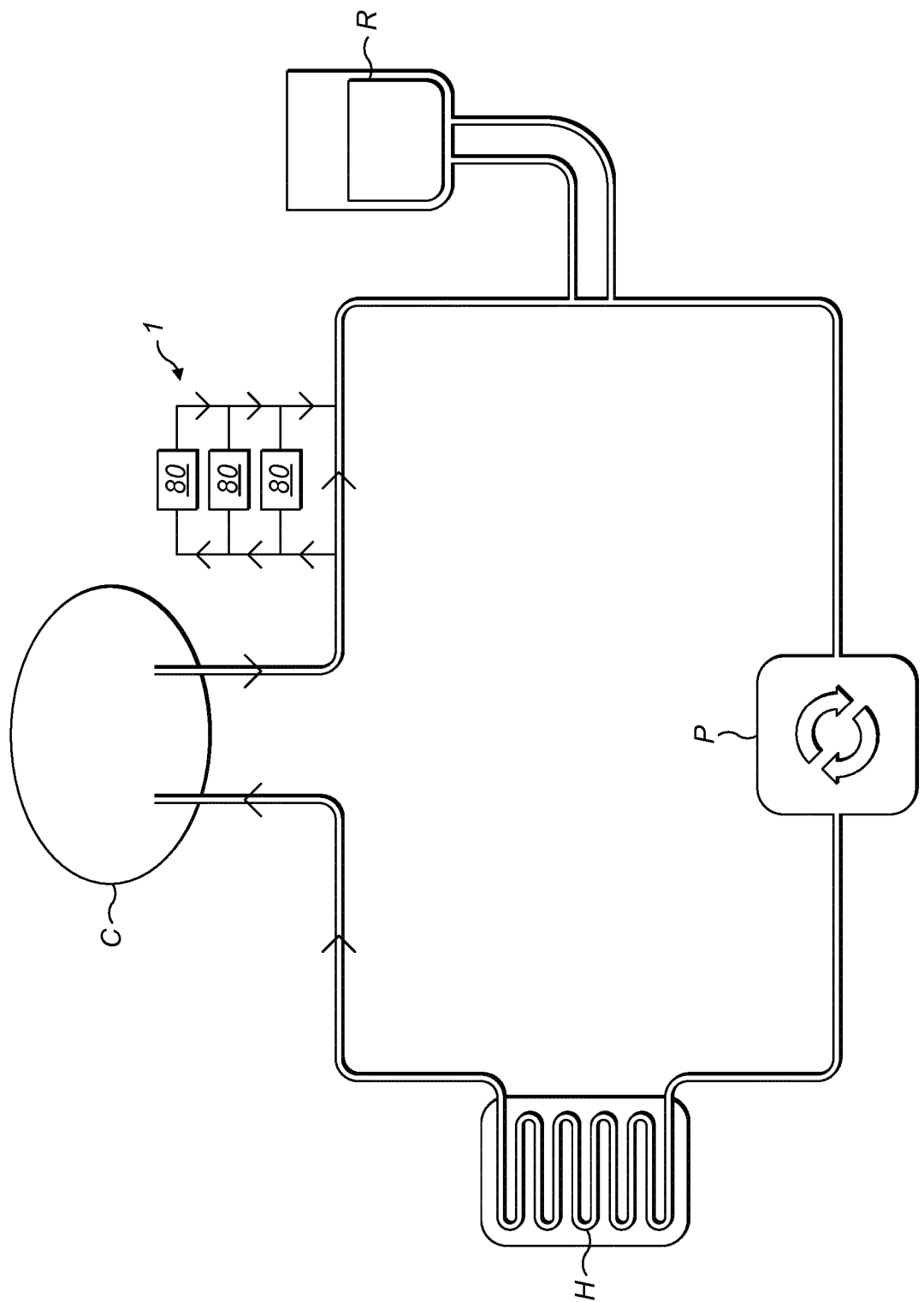
FIG. 7 is a schematic representation illustrating a recirculation system for use with an apparatus according to the present invention.

FIG. 7 shows a recirculation system comprising a reservoir R for the therapeutic fluid (e.g. a liquid formulation comprising a pharmaceutically active component), a pumping element P for circulating the fluid through the system and a heating element H for heating the fluid. The fluid enters a patient's body cavity C (e.g. the abdominal cavity, bladder, etc.), contacts the areas to be treated within said cavity and exits the cavity to return into the recirculation system. Ideally, the apparatus 1 according to the present invention is arranged and configured so as to monitor the fluid as it exists the patient's body cavity.

FIG. 1A illustrates the plurality of fluid sampling loops (A, B, and C) of the present invention prior to sampling. The plurality of fluid sampling loops are closed and the hyperthermic chemotherapy treatment fluid proceeds from a fluid source to the body cavity without entering the plurality of fluid sampling loops. Fluid continuously recirculates within the closed system into and out from the body cavity. The closed system provides a means to ensure that the body cavity is constantly washed with recirculating fluid during the procedure.

Figure 1B:
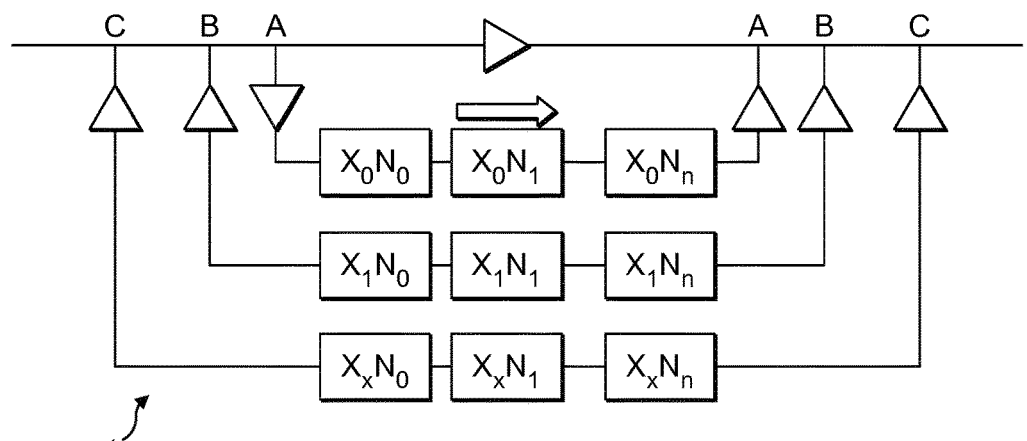
Figure 1C:
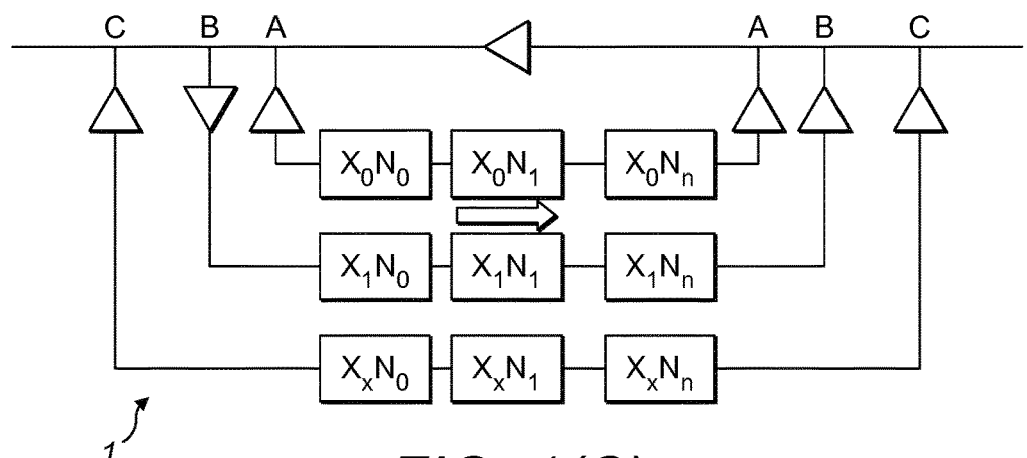

FIG. 1B illustrates an embodiment of the present invention in which a first sampling loop (A) has been opened to sample the recirculating hyperthermic chemotherapy treatment fluid at a first time point ($X_0$) prior to the application of the chemotherapeutic agent. As the fluid progresses through the first sampling loop (A) it encounters at least one filtration element. In the embodiment of FIG. 1B, there are at least three filters provided in series ($X_0N_0$, $X_0N_1$ to $X_0N_n$). The filters are adapted to capture cells, biological materials, and/or particles in the fluid. These filtration elements may be adapted to capture cells, biological materials, and/or particles such as tumour cells circulating in the fluid. At the end of a certain time period, the first sampling loop (A) is closed to prevent further entry of fluid. FIG. 1C illustrates a later time point ($X_1$) during a hyperthermic chemotherapy treatment procedure. At this time point the chemotherapeutic agent has been applied to the fluid circulating in the body cavity. A second sampling loop (B) opens at this time point ($X_1$) and fluid containing the chemotherapeutic agent is allowed to enter the second sampling loop (B). As for the first sampling loop, the fluid passes through at least one filtration element. In the embodiment of FIG. 1C, there are at least three filters provided in series ($X_1N_0$, $X_1N_1$ to $X_1N_n$) contained within the second sampling loop (B). At the end of a certain time period, the second sampling flow loop is closed to prevent further entry of fluid. It is envisaged that several fluid sampling loops may be used to sample the fluid at different time points during application of the chemotherapeutic agent to the body cavity.

Figure 1D:
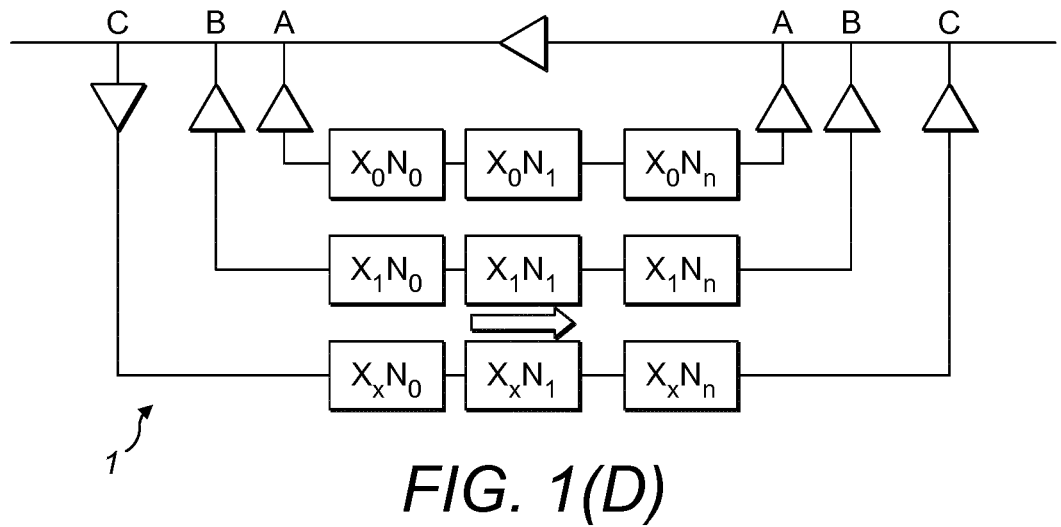

FIG. 1D illustrates further sampling of the fluid at a later time point ($X_x$). In one embodiment, this may be after application of the chemotherapeutic agent and during the flushing of the body cavity immediately prior to suturing and closure of the body cavity. In the embodiment of FIG. 1D, there are at least three filters provided in series ($X_2N_0$, $X_2N_1$ to $X_2N_n$) contained within a third sampling loop (C) which can be used to capture cells, biological materials, and/or particles in the fluid at the third time point $X_2$. At the end of a certain time period, the third sampling flow loop is closed to prevent further fluid entering the third sampling loop.

In one embodiment, the apparatus may have an interface means to connect the apparatus to a fluid flow system. The interface means may be adapted to allow the apparatus to be connected and disconnected without stopping a continuous flow and/or recirculation of the fluid in the fluid flow system. Therefore, the apparatus can be connected and disconnected without interruption of the procedure and samples can be analysed during a procedure over several time points.

In one embodiment, the plurality of fluid sampling loops may be formed from tubing or piping that creates a flow loop in to which a portion of the recirculating fluid is directed and flows through a given sampling loop such that it is returned to the fluid flow system upstream from the point at which it enters the sampling loop.

In one embodiment, the plurality of fluid sampling loops may each comprise a means for opening and closing each of the plurality of fluid sampling loops. The means for opening an closing each of the plurality of fluid sampling loops may be at least one clamp and/or at least one valve, such as a one way valve, that is opened and closed at predetermined time points. Therefore, fluid is prevented from entering a sampling loop until the appropriate time point and the cells, biological materials, and/or particles in the fluid can be sampled by different fluid sampling loops at different time points.

In one embodiment, the apparatus comprises a means to prevent reverse flow in a fluid sampling loop. The means for preventing reverse flow may be at least one clamp and/or at least one valve.

In one embodiment the apparatus may comprise a control means for controlling the opening and closing of the fluid sampling loops. The control means may operate to allow recirculating fluid to enter a given fluid sampling loop at a predetermined time point and allow fluid flow through a given fluid sampling loop for a predetermined period of time.

In certain embodiments, the characteristics of the different filtration elements such as the chosen filtration membrane and the mesh density should be as similar as possible between the filtration elements at the same position in each of the fluid sampling loops in order to obtain comparative results between different time points.

In certain embodiments, the different filtration elements with different properties can be positioned in series in the plurality of fluid sampling loops. For example, in one embodiment, certain filtration elements may be positioned to prevent blockage of the filtration elements further along in the series. In another embodiment, the filters may be differentially selective. In yet another embodiment, the diameter of the plurality of filtration elements which are arranged in series increases from a first filter of the plurality of filters to a last filter of the plurality of filters. In one embodiment, it is preferred that the plurality of fluid sampling loops contain the same filters in the same order in order to produce comparable samples at different time points.

In other embodiments, the filtration elements may be arranged in series and/or parallel within one or more fluid sampling elements. Certain fluid sampling loops may comprises sets of filtration elements arranged in parallel such that there are sub fluid sampling loops arranged within a fluid sampling loop.

In certain embodiments, the plurality of filters in each of the plurality of fluid sampling loops allows for the identification of viable cells at the different stages of a hyperthermia treatment in order to quantify the effectiveness of a surgical procedure in removing tumour cells from the body cavity.

In certain embodiments, the filtration elements can be removed from the apparatus individually such that the cells, biological materials, and/or particles captured by the filters can be analysed. In another embodiment, the filtration elements can be removed from the apparatus individually during recirculation of the fluid. For example, after a certain flow loop has closed and the fluid is no longer flowing through that flow loop, the filtration elements of that flow loop may be removed and the cells, biological materials, and/or particles trapped on the filter analysed. Therefore, the analysis of the cells, biological materials, and/or particles is possible while the fluid continues to recirculate during the procedure.

The filtration elements may comprise a filter housing with a fluid entry aperture and a fluid exit aperture. The filter may be arranged within the filter housing such that fluid must pass through the filter in order to exit the filter housing through the fluid exit aperture.

In one embodiment, the filtration elements may comprise connection means that allow reversible connection of the filtration elements to the fluid sampling loops. The connection means may be located on opposing sides of a filtration element such that the entire filtration element is removable from the fluid path of the fluid sampling loops. The connection means may comprise a snap-fit system or screw fit system. Suitable connection means are advantageous as it is important to handle the apparatus used to perform a HIPEC procedure carefully as the chemotherapeutic agents in the fluid used for recirculation are regarded as high risk toxic biohazard chemicals.

Prior to disconnecting the filtration elements from a sampling loop, the filter may be flushed. One purpose of flushing the filter may be to reduce the presence of toxic and potentially harmful chemicals in the filtration elements, for example the chemotherapeutic agent used in a HIPEC procedure.

Figure 2:
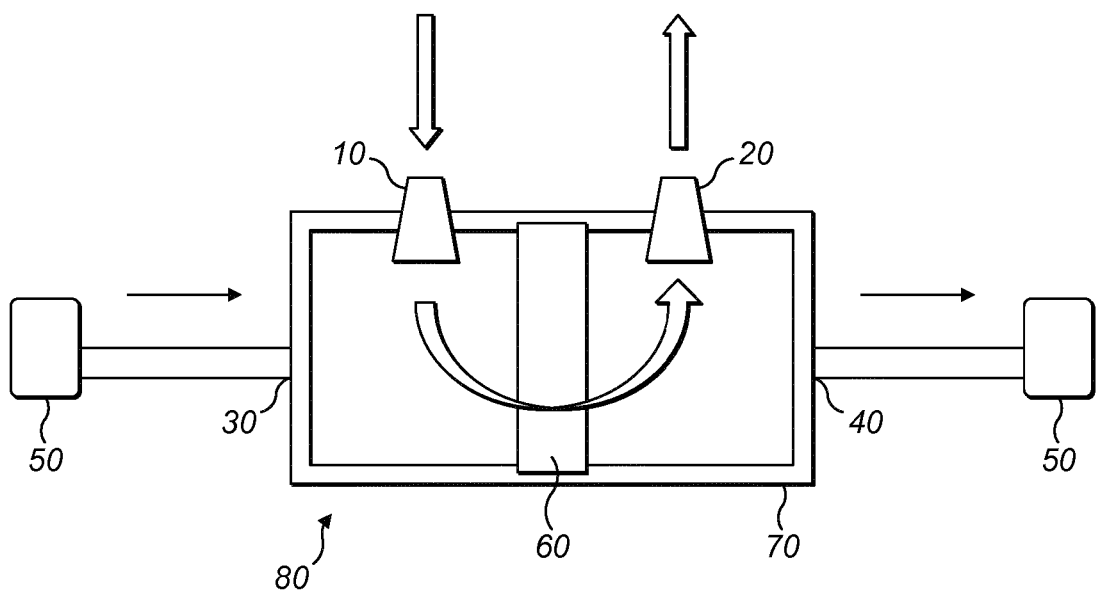
FIG. 2 is a schematic representation illustrating an embodiment of the filter flushing system.

In the embodiment of FIG. 2, the filtration element 80, which comprises filter housing 70 and filter 60, further comprises flushing inlet 10 and flushing outlet 20. The filtration element 80 is located between connection means 50 such that it can be removed from a sampling loop. The direction of fluid flow is shown in FIG. 2 is such that fluid flows into the filter housing 70 via the fluid entry aperture 30 and exits the filter housing 70 by the fluid exit aperture 40. The flushing inlet 10 is positioned prior to the filter 60 in the filter housing 70 and the flushing outlet is positioned after the filter 60, as defined by the direction of the fluid flow.

In the embodiment of FIG. 2, flushing occurs by passing a fluid through the flushing inlet 10 which passes through the filter 60 and out of the flushing outlet 20. Prior to flushing fluid enters the filter housing 70 via fluid entry aperture 30 and fluid exits the filter housing 70 via the fluid exit aperture 40. Prior to flushing these apertures can be blocked or closed such that the fluid used for flushing will only pass through the filter 60 and exit via the flushing outlet.

Figure 3:
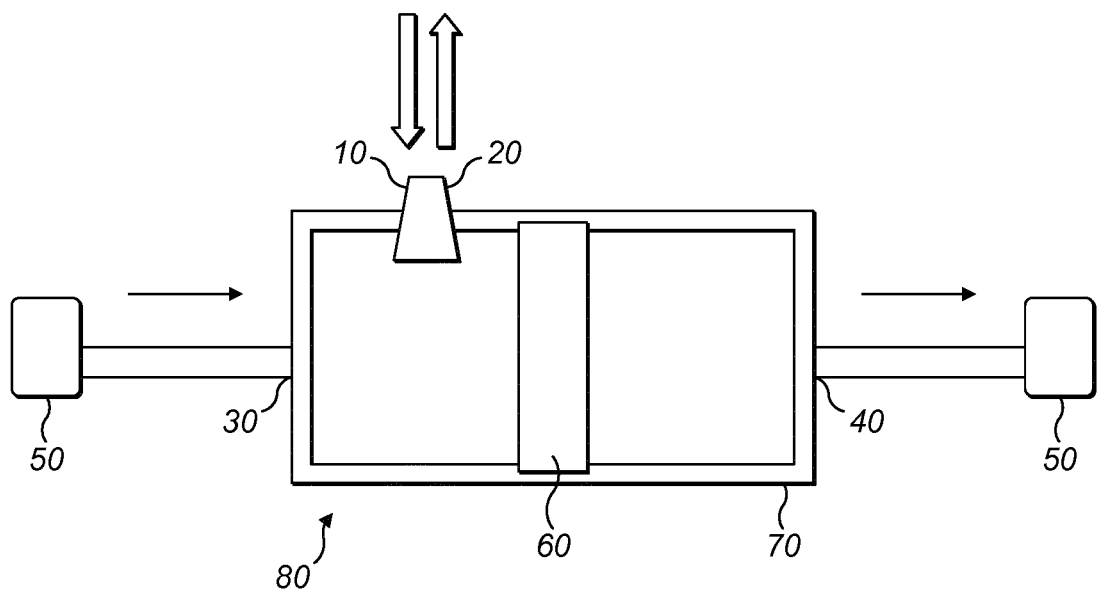
FIG. 3 is a schematic representation illustrating an alternative embodiment of the filter flushing system.

In the embodiment of FIG. 3, the filtration element 80 also comprises a fluid entry aperture 30, a fluid exit aperture 40, a filter 60, and a filter housing 70. The filtration element 80 is also positioned between opposing connection means 50. However, in this embodiment, the flushing inlet 10 and the flushing outlet 20 are formed from the same aperture. In this embodiment, the single flushing inlet 10 and flushing outlet 20 aperture are located prior to the filter 60 to form a dual flushing inlet and outlet, as defined by the direction of the fluid flow.

Figure 4:
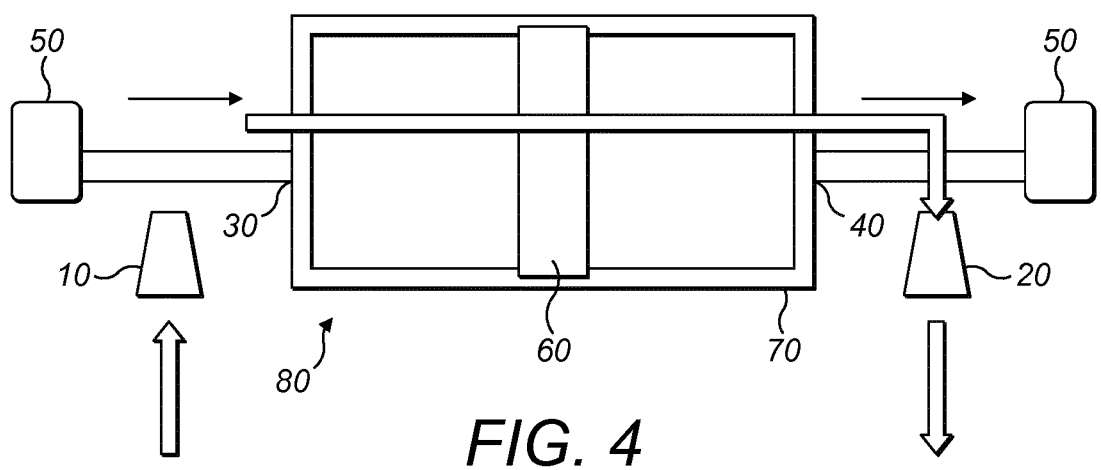
FIG. 4 is a schematic representation illustrating a further alternative embodiment of the filter flushing system.

In the embodiment of FIG. 4, the flushing inlet 10 and flushing outlet 20 are positioned between the connection means 50 and the filtration element 80. The flushing inlet 10 is located between a connection means 50 and the fluid entry aperture 30 and the flushing outlet 20 is located between the fluid exit aperture 40 and a connection means 50.

Figure 5:
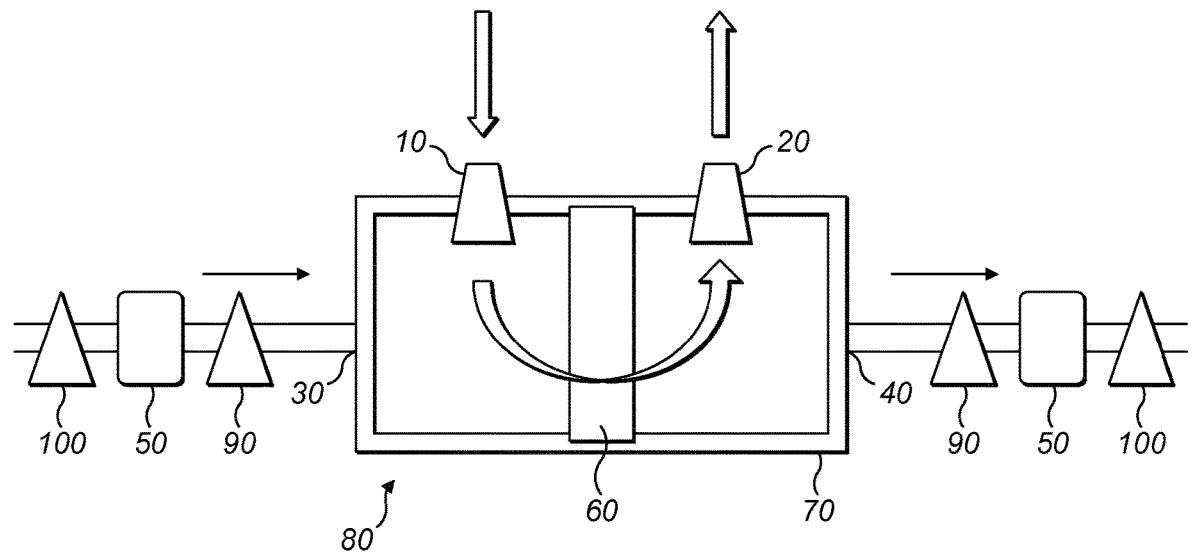
FIG. 5 is a schematic representation illustrating a further adaptation of the embodiment of the filter flushing system shown in FIG. 2.

The embodiment of FIG. 5 comprises a filtration element and connection means as arranged in FIG. 2. However, this figure additionally illustrates the clamps or non-return valve 90 which may be used to block or close the fluid entry aperture 30 and fluid exit aperture 40 to prevent re-flow during flushing and clamps 100 to prevent fluid escape during detachment of the connection means and removal of the filtration element 80 from the sampling loop.

Figure 6:
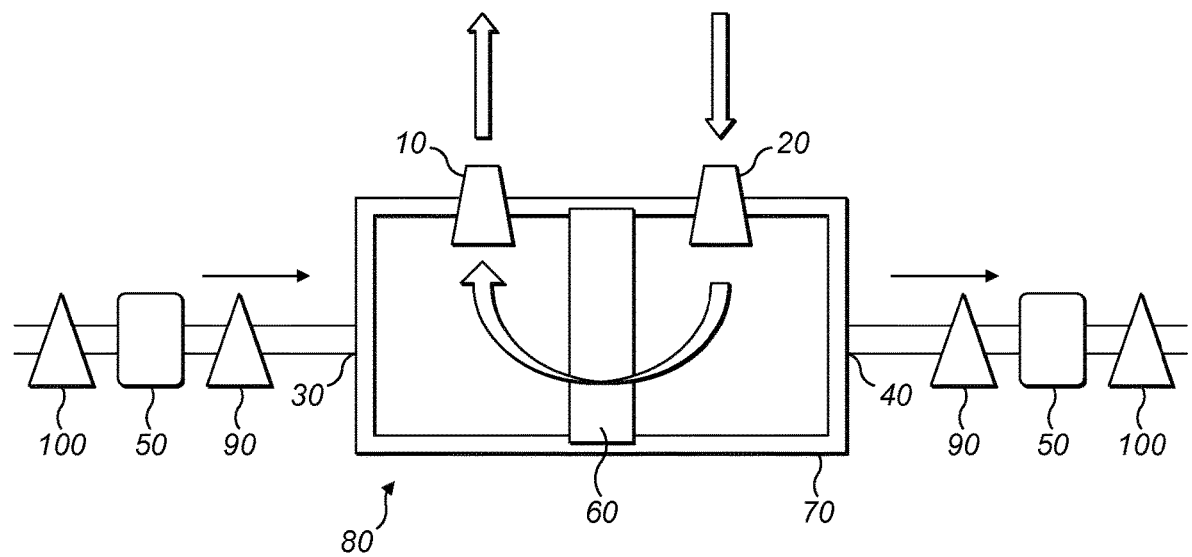
FIG. 6 is a schematic representation illustrating an alternative further adaptation of the embodiment of the filter flushing system.

FIG. 6 shows a different arrangement to the embodiment of FIG. 5 in which the flushing inlet 10 and flushing outlet 20 are reversed such that a reverse flow (opposite to regular flow direction during filtration) is used to flush the filter 60. A reverse flow may allow for sample collection without detaching the filtration element 80 from the system in order to maintain a closed system. In such an embodiment, the connection means 50 may not be required.

The invention claimed is:

1. An apparatus for monitoring cells, biological materials, and/or particles in a fluid flow system comprising a plurality of fluid sampling loops arranged substantially in parallel adapted to allow the fluid to enter each of the plurality of fluid sampling loops sequentially at different time intervals, wherein each of the plurality of fluid sampling loops comprises at least one filtration element adapted to retain the cells, biological materials, and/or particles when the fluid passes through each of the plurality of fluid sampling loops, wherein the apparatus is configured to create a closed fluid flow recirculation system and wherein, in use, the apparatus is configured to create a fluid flow that recirculates the fluid into and out from a body cavity of a patient, wherein each of the plurality of fluid sampling loops comprise a means for opening and closing each of the plurality of fluid sampling loops, and characterized in that the apparatus further comprises a control means for controlling the opening and closing of the plurality of fluid sampling loops at predetermined time points.

2. An apparatus according to claim 1, wherein the means for opening and closing each of the plurality of fluid sampling loops comprises at least one clamp and/or at least one valve adapted to allow fluid to enter a given sampling loop only at a predetermined time point.

3. An apparatus according to claim 1, wherein the apparatus comprises at least one clamp and/or at least one valve adapted to prevent reverse fluid flow in the plurality of sampling loops.

4. An apparatus according to claim 1, wherein the system apparatus comprises a connection means adapted to allow connection and disconnection of the connection means from the fluid flow system without stopping a continuous flow and/or recirculation of the fluid in the fluid flow system.

5. An apparatus according to claim 1, comprising a flushing means.

6. An apparatus according to claim 5, wherein the flushing means comprises a flushing inlet and a flushing outlet.

7. An apparatus according to claim 6, wherein the at least one filtration element comprises the flushing inlet and the flushing outlet.

8. An apparatus according to claim 7, wherein the at least one filtration element comprises a dual flushing inlet and outlet formed from a single aperture.

9. An apparatus according to claim 6, wherein the flushing inlet is located upstream of the at least one filtration element in the direction of the fluid flow and the flushing outlet is located downstream of the at least one filtration element in the direction of the fluid flow.

10. An apparatus according to claim 6, wherein the flushing inlet is located downstream of the at least one filtration element in the direction of the fluid flow and the flushing outlet is located upstream of the at least one filtration element in the direction of the fluid flow.

11. An apparatus according to claim 6, wherein one or more of the plurality of fluid sampling loops comprises a plurality of filtration elements arranged in series.

12. An apparatus according to claim 11, wherein a diameter of the plurality of filtration elements and/or a diameter of the pore size of the filtration elements is arranged in series increasing from a first filter of the plurality of filtration elements to a last filter of the plurality of filtration elements.

13. An apparatus according to claim 11, wherein each of the plurality of filtration elements comprises a respective flushing inlet and a respective flushing outlet.

14. An apparatus according to claim 11, wherein each of the plurality of filtration elements comprises connecting means such that each of the filtration elements can be independently connected to and disconnected from a sampling loop.

15. An apparatus according to claim 1, wherein the fluid is in a closed recirculation system.

16. An apparatus according to claim 1, wherein the fluid is a therapeutic recirculation fluid in a therapeutic recirculation system.

17. An apparatus according to claim 1, wherein the fluid is a hyperthermia therapeutic recirculation fluid in a hyperthermia therapeutic recirculation system.

18. An apparatus according to claim 1, wherein the fluid is hyperthermic chemotherapy recirculation fluid in a hyperthermic chemotherapy recirculation system.

19. An apparatus according to claim 1, wherein the fluid is hyperthermic intraperitoneal chemotherapy recirculation fluid in a hyperthermic intraperitoneal chemotherapy recirculation system.

20. An apparatus according to claim 1, wherein a first fluid sampling loop of the plurality of fluid sampling loops is adapted to allow the fluid flow to enter the first fluid sampling loop after surgery and prior to application of a therapeutic agent to the fluid.

21. An apparatus according to claim 20, wherein a second fluid sampling loop of the plurality of fluid sampling loops is adapted to allow the fluid flow to enter the second fluid sampling loop after application of the therapeutic agent to the fluid.

22. An apparatus according to claim 21, wherein a third fluid sampling loop of the plurality of fluid sampling loops is adapted to allow the fluid flow to enter the third fluid sampling loop during a flushing procedure after completion of the application of the therapeutic agent.

23. A filtration element adapted for use with the apparatus of claim 1.

* * * * *